US008815557B2

(12) United States Patent
Lee et al.

(10) Patent No.: US 8,815,557 B2
(45) Date of Patent: Aug. 26, 2014

(54) COMPOSITIONS AND METHODS FOR REFOLDING OF DENATURED PROTEINS

(75) Inventors: Raphael C. Lee, Chicago, IL (US);
Annie Kuo, Salt Lake City, UT (US);
Hanne Gissel Hyldkrog, Trige (DK);
Florin Despa, North Riverside, IL (US);
Devkumar Mustafi, Chicago, IL (US)

(73) Assignee: University of Chicago, Chicago, IL (US)

( * ) Notice: Subject to any disclaimer, the term of this patent is extended or adjusted under 35 U.S.C. 154(b) by 1941 days.

(21) Appl. No.: 11/483,898

(22) Filed: Jul. 10, 2006

(65) Prior Publication Data

US 2007/0031955 A1    Feb. 8, 2007

Related U.S. Application Data

(60) Provisional application No. 60/697,665, filed on Jul. 8, 2005.

(51) Int. Cl.
*C12N 9/00* (2006.01)

(52) U.S. Cl.
USPC .......................................................... 435/183

(58) Field of Classification Search
CPC ...... C07K 1/1136; C07K 14/00; A23L 1/296; A23L 1/3053; C08L 71/02; C08L 2666/26
See application file for complete search history.

(56) References Cited

U.S. PATENT DOCUMENTS

| 4,093,606 | A | * | 6/1978  | Coval           | 530/390.5 |
| 4,474,571 | A |   | 10/1984 | Lasley          |           |
| 4,474,752 | A |   | 10/1984 | Haslam          |           |
| 5,593,844 | A | * | 1/1997  | Carlsson et al. | 435/7.1   |
| 5,728,804 | A |   | 3/1998  | Sharma          |           |
| 6,489,450 | B2|   | 12/2002 | Randolph        |           |

FOREIGN PATENT DOCUMENTS

JP    02-078629    3/1990

OTHER PUBLICATIONS

Yoshimot N et al. 2003. Artificial chaperone-assisted refolding of bovine carbonic anhydrase using molecular assemblies of stimuli-responsive polymers. Biomacromolecules 4: 1530-1538.*
Balta Calleja FJ et al., ed. 2000. "Introduction and Plan," in Block copolymers (Marcel Dekker, New York); at p. 1.*
Cleland, et al., *Bio/Technology*, "Polyethylene Glycol Enhanced Protein Refolding," 10:1013-1019 (1992).
Nguyen, et al., *Protein Expression Purif.*, "Overproduction and Purification of $\sigma^{32}$, the *Escherichia coli* Heat Shock Transcription Factor," 4:425-433 (1993).
Rozema and Gellman, *J. Amer. Chem. Soc.*, "Artificial Chaperones: Protein Refolding via Sequential Use of Detergent and Cyclodextrin," 117:2373-2374 (1995).
Sawhney et al., *Macromolecules*, "Bioerodible Hydrogels Based on Photopolymerized Poly(ethylene glycol)-co-poly($\alpha$-hydroxy acid) Diacrylate Macromers," 26:581-587 (1993).
Zardeneta and Horowitz, *J. Biol. Chem.*, "Micelle-assisted Protein Folding," 267(9):5811-5816 (1992).

* cited by examiner

*Primary Examiner* — Lora E Barnhart Driscoll
(74) *Attorney, Agent, or Firm* — Brinks Gilson & Lione

(57) ABSTRACT

Compounds and methods for refolding of proteins in an aqueous solution. In particular, biocompatible multiblock copolymer surfactants such as poloxamers, meroxapols, poloxamines, or polyols are used to catalyze proper refolding without changing the protein composition, and restore the protein to its native conformation and native biological function. The methods can be practiced both in vivo and in vitro. The biocompatible multiblock copolymer surfactants can be used for renaturation of recombinantly expressed proteins, and for renaturation of proteins that are unfolded due to heat, irradiation, mechanical shearing, electrical shock, frostbite, chemical stress, and other abiotic or biotic stresses.

17 Claims, 4 Drawing Sheets

US 8,815,557 B2

COMPOSITIONS AND METHODS FOR REFOLDING OF DENATURED PROTEINS

RELATED APPLICATIONS

This application claims priority to U.S. Provisional Application No. 60/697,665, filed Jul. 8, 2005.

FEDERALLY SPONSORED RESEARCH OR DEVELOPMENT

This invention was made in part with government support under grant number GM 64757 awarded by the National Institutes of Health. The Government has certain rights in this invention.

TECHNICAL FIELD

The field of the present invention is protein biochemistry, in particular, the renaturation (refolding) of biologically active proteins that have become denatured.

BACKGROUND OF THE INVENTION

Protein function is dependent on its three-dimensional structure. When a protein is synthesized in a mammalian cell, it first appears essentially as a linear polypeptide chain. The immature chain then folds under appropriate cellular conditions (pH, ionic strength, etc.). Most globular proteins exhibit complicated three-dimensional folding described as secondary, tertiary, and quaternary structures. Sometimes the protein folding occurs with the help of protein folding catalysts called molecular chaperones, which are proteins themselves. Out of thousands of possible three dimensional shapes, an average mature protein assumes only one conformation, which is often referred to as the native structure of the protein. This conformation of the protein molecule is rather fragile. Any alteration in the protein's native structure may lead to loss of the protein's biological activity, a phenomenon called denaturation. Since the native structure is maintained mostly by weak forces (hydrogen bonding, electrostatic and hydrophobic interactions), proteins can easily be denatured by small changes in their environment. Thus protein denaturation occurs in their purification, storage, use, and transport. A given protein sample may therefore contain appreciable amounts of denatured, inactive protein besides the active, functional form.

Extensive unfolding sometimes causes precipitation of the protein from solution. Denaturation is defined as a major change from the original native state without alteration of the molecule's primary structure, i.e., without cleavage of any of the primary chemical bonds that link one amino acid to another. Treatment of proteins with strong acids or bases, high concentrations of inorganic salts or organic solvents (e.g., alcohol, chloroform, or guanidine hydrochloride), heat, mechanical shearing, or irradiation, all produce denaturation to a variable degree. Loss of three-dimensional structure usually produces a loss of biological activity. A denatured enzyme is often without catalytic function.

With the growth of the biotechnology industry and the increased production of recombinant proteins, interest in the mechanisms by which a protein adopts its native structure has increased dramatically. A number of therapeutic proteins are currently being produced by recombinant DNA technology, by incorporating a copy of the human gene encoding a particular protein into a rapidly dividing host cell such as a bacterium. The genes are then transcribed into mRNA and translated into protein by the host cell.

Recombinant proteins overexpressed in *Escherichia coli* are often accumulated as insoluble particles called inclusion bodies. Since proteins in inclusion bodies are usually inactive, they must be solubilized by a denaturing agent and refolded to recover their native steric structures having biological activities. In bioprocesses it is important to obtain a high refolding efficiency and high throughput at high protein concentrations.

Various methods for renaturing denatured proteins in solution have been disclosed. Renaturation of the denatured proteins is accomplished with varying success, and occasionally with a return of biological function, by exposing the denatured protein to a solution that approximates normal physiological conditions. Renaturation of proteins using cyclodextrins in a detergent-free liquid medium has been described in U.S. Pat. No. 5,728,804. A high pressure-based method for the refolding of denatured proteins in solution was provided in U.S. Pat. No. 6,489,450.

Renaturation (refolding) processes can involve dispersing the protein inclusion bodies in a buffer in the presence of "refolding aids," which can interact with the protein to enhance its renaturation. J. L. Cleland et al., *Biotechnology*, 10, 1013 (1992), reported that polyethylene glycol enhances refolding yields. Various sugars and detergents have also been employed in refolding. G. Zardeneta et al., *J. Biol. Chem.*, 267, 5811 (1992); L. H. Nguyen et al., *Protein Expression Purif.*, 4, 425 (1993). Recently, D. Rozema et al., *J. Amer. Chem. Soc.*, 117, 2373 (1995), reported that sequential complexation of denatured carbonic anhydrase B with a quaternary amine detergent, CTAB, followed by addition of beta-cyclodextrin to the complex, caused reactivation of the enzyme. None of these methods have been used to refold proteins inside cells, either in vitro or in vivo.

A continuing need exists for methods and compositions for renaturation of denatured proteins. It is particularly important to discover non-toxic compounds and methods that aid renaturation of proteins in an aqueous solution. Such protein folding aids and methods should be inexpensive, non-toxic, and easily administered to the denatured protein sample.

BRIEF SUMMARY OF THE INVENTION

The present invention provides compositions and methods for renaturing ("refolding") a denatured ("unfolded" or aggregated) protein comprising contacting the protein with an amount of a biocompatible, multiblock copolymer surfactant (such as a poloxamer) effective to renature the protein. The denatured protein may be in solution, in a cell, and even in a tissue. The denatured protein may be partially or wholly in the form of suspended aggregates. In particular, this invention teaches that biocompatible, multiblock copolymer surfactants can be used to disaggregate denatured protein precipitates, catalyze proper refolding without binding to or changing the protein composition, and restore the protein to its native conformation and native biological function.

The method of the invention involves the use of a biocompatible, multiblock copolymer surfactant, for example a poloxamer, to potentiate the healing process by restoring protein structure and function. The present invention is based on the realization that a biocompatible, multiblock copolymer surfactant can refold denatured proteins. Thus, the present invention has potential for treating damaged tissue. The present invention increases protein renaturation in damaged tissue by applying pharmaceutical compositions containing a biocompatible, multiblock copolymer surfactant to the damaged tissue. The biocompatible, multiblock copolymer surfactant can be administered intravenously, intramuscularly, subcutaneously or topically.

The method provides for renaturing a denatured protein, and includes the steps of contacting the denatured protein with an amount of biocompatible multiblock copolymer surfactant for a time and temperature sufficient to renature the protein into its native structure.

The method provides for renaturation of a denatured protein, which includes the steps of preparing an aqueous solution comprising a biocompatible multiblock copolymer surfactant and contacting the protein with the aqueous solution for a time sufficient to renature the protein, where the denatured protein was denatured mechanically, by low temperature, suboptimal pH, addition of detergents, high salt concentration, use of chaotropic agents, or chemically cleaving disulfide bonds.

The present invention can be used, but not limited, to treating tissue damaged by thermal burns, electrical shock, frostbite, chemical stresses, and other stresses that cause protein denaturation in animals and humans. The stresses can be biotic, abiotic, or combinations of both.

The present invention can be used for restoring the biological activity to a denatured protein. Denaturation of the protein could have occurred mechanically, by low temperature, high temperature, suboptimal pH, addition of detergents, high salt concentration, use of chaotropic agents, or chemically cleaving disulfide bonds.

In one embodiment, the methods of the present invention are practiced in solution, such as an aqueous medium. Upon refolding, the protein can be employed for its end use in solution, or it can be recovered from solution, either in combination with the biocompatible, multiblock copolymer surfactant or in essentially pure form. If desired, the biocompatible, multiblock copolymer surfactant can be removed from the solution. The protein can be recovered by freeze drying, filtration, chromatography and the like.

In another embodiment, the methods and the compounds of the invention can be used for proper folding of recombinant proteins that have been produced using translation vehicles (e.g., bacteria, insects, etc.).

DETAILED DESCRIPTION OF THE INVENTION

Figure 1:
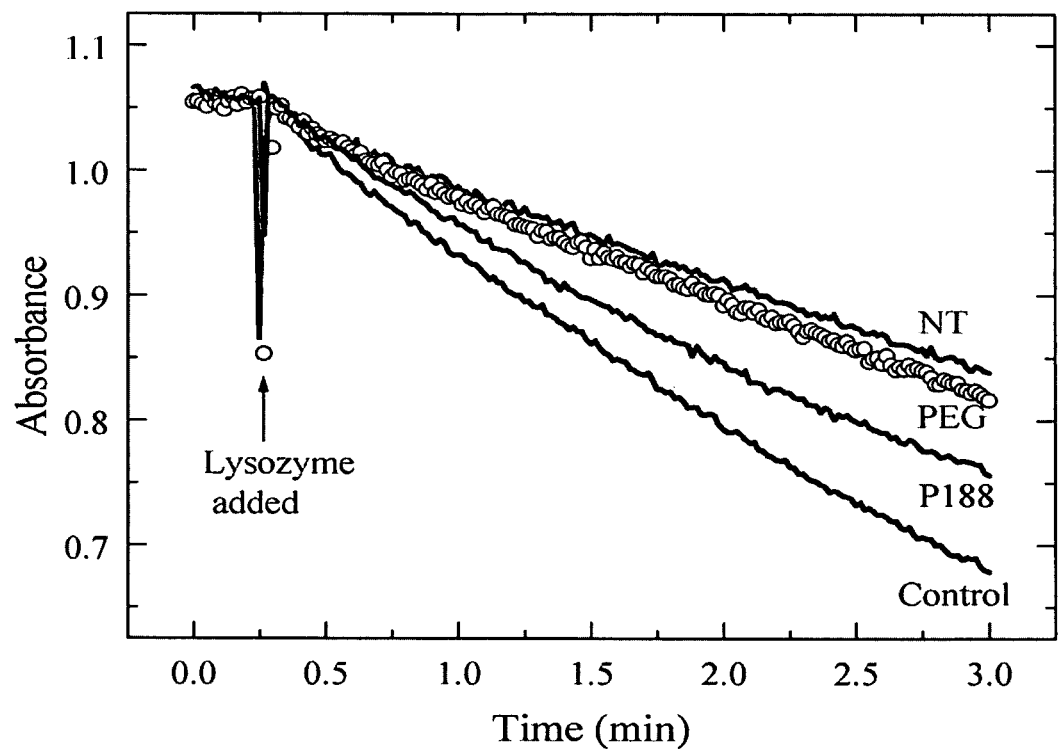
FIG. 1 shows the kinetics of change in absorbance of *Micrococcus lysodeikticus* (MCLD) cells at 700 nm in the presence of HEWL (heat denatured hen egg white lysozyme). Enzyme solutions were heated at 90° C. for 40 min followed by cooling to 25° C. for 30 min. Then a biocompatible, multiblock copolymer surfactant (here the poloxamer P188) or polyethylene glycol (PEG) was added at a 2:1 molar ratio of polymer:protein and the assay was started as quickly as possible. Untreated samples (NT) underwent the same heating-cooling cycle but with the addition of buffer, without P188 or PEG. The control sample was kept at 25° C. throughout. The reaction was initiated by addition of HEWL to the suspension of MCLD after 15 sec, as indicated by the arrow.

It is to be understood that this invention is not limited to the particular methodology, protocols, patients, or reagents described, and as such may vary. It is also to be understood that the terminology used herein is for the purpose of describing particular embodiments only, and is not intended to limit the scope of the present invention, which is limited only by the claims.

The present invention is based on the inventors' discovery that multiblock copolymer surfactant can refold and stabilize proteins. Although not intending to be bound by any theory of action, it is believed that the multiblock copolymer surfactant's action is primarily as an artificial protein chaperone. The amphiphilic nature of multiblock copolymer surfactants may allow them to act as an artificial chaperone in solution. One possibility is that the exposed hydrophobic portion of the biocompatible, multiblock copolymer surfactant is attracted to the hydrophobic portion of the denatured protein and displaces solvent, allowing the native structure to be regained. Low molecular weight biocompatible, multiblock copolymer surfactant allows them ready access to and from the interior of the protein during refolding.

The methods and compositions of the present invention may be used in the preservation of biomaterials that contain protein such as human cells, animal cells, plant cells, cell lines, tissues, organs, and the like. When a biomaterial is preserved, its viability is maintained in vitro for an extended period of time, such that the biological activity of the biomaterial is at least partially restored.

Examples of biomaterials that may be preserved using the present invention include, but are not limited to, organs, such as heart, kidneys, lungs, and livers; cells and tissues such as hematopoietic and embryonic stem cells, bone marrow, embryos, platelets, osteoblasts, spermatozoa, granulocytes, red blood cells, dendritic cells, oocytes; and various animal cell lines established in tissue culture. The invention is particularly useful for difficult to preserve biomaterials including nucleated living cells, and in particular, mammalian cells such as fibroblasts, hepatocyces, chondrocytes, keratinocytes, islets of Langerhans, granulocytes, and hematopoietic and embryonic stem cells. In addition to the preservation of human biomaterials, the inventive compositions and methods may also be employed in veterinary applications, and for preservation of plant and marine tissues.

Multiblock Copolymer Surfactant

Various types of multiblock copolymer surfactant may be used for practicing the invention.

"Multiblock copolymer surfactant" includes any copolymers that are surface active agents that are prepared by the sequential addition of two or more alkylene oxides to a low molecular weight water soluble organic compound containing one or more active hydrogen atoms. Four groups of surface active copolymers are of particular importance with regard to the present invention: poloxamers, meroxapols, poloxamines, and polyols. Poloxamers are particularly preferred. All four groups of non-ionic surface active agents are alike in that they derive their solubility in water from hydrogen bond formation between the many oxygen atoms on the copolymer and protons in the water.

Poloxamers are typically synthesized by the sequential addition of propylene oxide, followed by ethylene oxide, to propylene glycol. Poloxamers change from water-soluble to water-insoluble polymer as the molecular weight goes above 750 Daltons. The family of poloxamers consists of differing ratios of hydrophilic (polyoxyethylene) and hydrophobic (polyoxypropylene) chains. Poloxamers with a molecular weight of at least 2,000 and not more than 60,000 Daltons are typically used in this invention. This molecular weight range maintains the appropriate solubility of the poloxamer in water while minimizing or eliminating any potential toxicity. The poloxamer's hydrophobic group typically has a molecular weight of approximately 2,000-20,000 Daltons, and its hydrophilic groups typically has a molecular weight of approximately 45-95% by weight of the poloxamer. The relative amounts of hydrophile and the molecular weight of the hydrophobe affect several of the poloxamer's properties, including its solubility in water and its interactions with hydrophobic groups, and the ranges taught in the present invention provide the maximum effectiveness currently known while minimizing or eliminating toxicity.

In one preferred embodiment, polyoxyethylene-polyoxypropylene block copolymers such as, e.g., the Pluronic™ series, the Synperonic™ series, Emkalyx™, Lutrol™, Supronic™, and others can be used. These proprietary polymers are available from BASF (Germany). The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407.

More preferably, poloxamer 188 (P188, MW=8400 g/mol) is used. The ratio of polyoxyethylene:polyoxypropylene:polyoxyethylene is 80:27:80. Functional equivalents of P188, i.e., similar non-ionic surfactants from the family of poloxamers, could be used for practicing the invention.

Macromers having a poly(ethylene glycol) central block, extended with oligomers of α-hydroxy acids such as oligo(d, l-lactic acid) or oligo(glycolic acid) and terminated with acrylate groups can also be used (See Sawhney et al., *Macromolecules*, 26: 581-589 (1993), which is incorporated herein by reference). Another synthesized biodegradable block copolymer that can be used in the present invention is disclosed in Japanese Patent No. 2-78629 (which is incorporated herein by reference). These copolymers are synthesized by transesterification of poly(lactic acid) (PLA) or poly(lactic acid)/glycolic acid (PLA/GA) and poly(ethylene glycol) (PEG).

Meroxapol are synthesized by the sequential addition of ethylene oxide, followed by propylene oxide, to propylene glycol. As opposed to the poloxamers, which are terminated by two primary hydroxyl groups, the meroxapols have secondary hydroxyl groups at the ends and the hydrophobe is split in two, each half on the outside of the surfactant. Compounds from the meroxapol series can be used for practicing the invention.

Poloxamines can also be used. Poloxamines are prepared from an ethylene diamine initiator. They are synthesized using the same sequential order of addition of alkylene oxides as used to synthesize the poloxamers. Structurally, the poloxamines differ from the other polymers in that they have four alkylene oxide chains, rather than two, since four active hydrogens are present in the initiator. They also differ from the other surfactants in that they contain two tertiary nitrogen atoms, at least one of which is capable of forming a quaternary salt. The poloxamines are also terminated by primary hydroxyl groups.

Polyols (such as Pluradot™ and Tetronic™) can also be used. For example, polyols can be prepared from a low molecular weight trifunctional alcohol, such as glycerine or trimethylpropane, which is oxyalkylated initially with a blend of propylene and ethylene oxides, but primarily with propylene oxide, to form the hydrophobe. This is followed by oxyalkylating with a blend of ethylene and propylene oxines, but primarily ethylene oxide, to form the hydrophile. This group of surfactants has three chains, one more than the poloxamer and meroxapol series, but one less than the poloxamine polymers.

Tetronic™ polymers are described in U.S. Pat. Nos. 4,474,751 and 4,474,752, which are incorporated herein by reference, and are available from BASF (Germany). Such polymers can be dissolved in an aqueous base with a desired pH, and the solution can be injected subcutaneously or intramuscularly. Upon injection into a physiological environment, the aqueous solution can form a semi-solid gel at body temperature. Tetronic 1077 (T1077; MW=15000 g/mol) is preferably used. T1077 is a tetrafunctional block copolymer surfactant terminating in primary hydroxyl groups.

The hydrophilic and hydrophobic chains of the surface active copolymers each have unique properties which contribute to the substances' biological activities. With regard to poloxamers in particular, the longer the hydrophilic polyoxyethylene chains are, the more water the molecule can bind. As these flexible chains become strongly hydrated they become relatively incompressible and form a barrier to hydrophobic surfaces approaching one another. The hydrophobic component of the poloxamers is typically large, weak and flexible.

The biocompatible, multiblock copolymer surfactant can be formulated into a composition through the use of a biocompatible carrier. Suitable carriers will depend on the environment surrounding the denatured proteins being refolded. "Biocompatibility" refers to compatibility with living cells, tissue or a living system by not being toxic, injurious, or physiologically reactive, and not causing immunological rejection.

The amount of biocompatible multiblock copolymer surfactant used for refolding of denatured proteins may vary. For in vitro applications the aqueous medium where the protein is refolded should contain about 0.1% to about 10% (w/v) of the biocompatible, multiblock copolymer surfactant. For treatment of injured subjects, it is contemplated that the amount of biocompatible multiblock copolymer surfactant administered to the subject should contain about 0.1% to about 10% (w/v) of the total amount that is administered to the subject. In preferred embodiments, the molar ratio of biocompatible, multiblock copolymer surfactant to denatured protein is in the range of approximately 10:1 to 0.1:1. More preferably, the molar ratio of biocompatible, multiblock copolymer surfactant to denatured protein is about 2:1.

Denatured proteins can be refolded in a wide range of solvents—but preferably are refolded in aqueous or aqueous/organic solvents. When the denatured proteins are in protein aggregates, the aggregates may not initially be solubilized by the solvent.

The denatured protein may be in solution or partially or wholly in the form of suspended aggregates, and the term "in an aqueous medium" encompasses all of these forms.

In general, it is necessary to establish contact between the biocompatible multiblock copolymer surfactant and the protein that needs to be preserved or renatured. In preferred embodiments, an aqueous solution that includes a biocompatible multiblock copolymer surfactant is prepared. Then the aqueous solution is used as a liquid medium for contacting the biocompatible multiblock copolymer surfactant with the denatured protein, and/or with the protein that needs to be stabilized in its native (renatured) form.

Once the biocompatible multiblock copolymer surfactant has established contact with protein that needs to be preserved or renatured, and has effectuated renaturing according to this invention, the biomaterials that need to be preserved can be prepared for storage in a preserved state.

Suitable aqueous solutions may be buffered to about pH 6-9. Any suitable buffer can be used, including Tris. Ideally, the aqueous solution but is free of other refolding aids, including other detergents, sugars or polyols, including polyethylene glycol.

The renaturing reaction occurs readily under essentially ambient temperatures (10° C.-40° C.), although higher temperatures may be employed for thermally-resistant proteins. After a sufficient period of time, e.g., about 30-90 minutes or longer, at least about 75% of the initial or theoretical activity of the enzyme is attained, and recoveries of up to 95-100% have been accomplished. In addition to enzymes, the invention can be used for renaturation of hormones, cytokines, or other proteins. In one embodiment of the invention, the denatured protein is suspended in an aqueous solution. The aqueous medium may be buffered to a pH of about 6.0-9.0, using buffering methods ordinarily known in the art. These methods may include addition of buffering compounds, e.g. Tris. Upon addition of the biocompatible, multiblock copolymer surfactant, refolding of the denatured protein is carried out for a period sufficient to refold a substantial amount of the protein, typically about 0.5-2 hours. The temperature can be varied, but is typically about room temperature (25° C.), preferably in the range of 15-40° C.

While in many instances one application of a multiblock copolymer surfactant will be sufficient, a skilled artisan will recognize that, in certain applications, repeated application of multiblock copolymer surfactant can be used to promote the renaturation and stabilization of denatured proteins.

The method provides for restoring the biological activity to a denatured protein. In preferred embodiments, the protein is an enzyme. The term "restoring the biological activity" of a denatured protein means restoration of at least 10% of the protein's native biological activity. Alternatively, percent biological activity can be any integer from 10% to 100%. More preferred embodiments include at least: 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a protein that has not been denatured.

The low poloxamer:protein ratios sufficient for the observed chaperone-like effect provides for a variety of industrial as well as medical applications. Poloxamers are relatively inexpensive and are commercially available. It is relatively easy to separate the poloxamers, if desired, from the refolded protein. This can be done, for example, by dialysis or gel filtration.

In one aspect, the present invention may be used to preserve a wide variety of foods, including meat, fish, vegetables, and fruits. The foods may either be processed or non-processed. The foods may be shelf foods (kept at room temperature), refrigerated foods, or frozen foods. So long as the foods include proteins, the methods of the present invention can be used for preservation of those foods.

"Non-animal foodstuff" as used herein refers to food that is typically not intended for animal consumption. For example, non-animal foodstuff includes food that is typically intended for consumption by humans. "Proteinaceous non-animal foodstuff" is non-animal foodstuff that includes proteins.

Stabilization and renaturation of proteins in non-animal foodstuff is beneficial when proteins in the food become denatured. Proteins in food can become denatured when the food is prepared, processed, packaged, transported, or stored. For example, treatment of the food with strong acids or bases, high concentrations of inorganic salts, detergents, suboptimal pH, solvents, low temperature, heat, mechanical shearing, or irradiation will produce denaturation of proteins in the food to a variable degree.

The food preservation method basically involves placing the food to be preserved in contact with a biocompatible multiblock copolymer surfactant. Although many different means may be used to provide the contact, it is preferred to establish contact between the food to be preserved and an aqueous solution that includes the biocompatible multiblock copolymer surfactant in a closed container. For food preservation, one preferred technique is to place the aqueous solution on a suitable absorbent material such as powders of protein, sugar dextran, cellulose, methylcellulose, ethylcellulose, gelatin, silicon dioxide, acidic aluminum and talc. Any other suitable absorbents which absorb multiblock copolymer surfactants and are also non-toxic may be used. The absorbent, including the absorbed aqueous solution, is then placed in contact with the food. Suitable containers include any number of plastic bags or containers.

It may also be beneficial, in addition to the biocompatible multiblock copolymer surfactant, to add certain high-molecular weight bio-preservation agents that are not taken up into the biomaterial that needs to be preserved. Such agents are raffinose, dextrans, and other large molecules that may be used extracellularly with the method of the invention to enhance the outcome of a particular preservation protocol.

It is contemplated that the methods of this invention could be used for the treatment of an injury that causes denaturation of proteins in a subject. Denaturation of proteins in a subject could be caused by various stresses. Such stresses could, for example, be abiotic or biotic (biochemical).

Accordingly, an amount of biocompatible multiblock copolymer surfactant effective to refold denatured proteins into their native structures could be administered to an injured subject. The biocompatible multiblock copolymer surfactant should be administered for an amount of time sufficient to refold the denature proteins into their native structures. The administration of the biocompatible multiblock copolymer surfactants could be topical, vascular, or through other methods commonly known in the art. The biocompatible multiblock copolymer surfactant could be delivered using accepted pharmaceutical carriers. In some instances, repeated applications of multiblock copolymer surfactants may be needed to promote protein renaturation and subject's healing.

It is contemplated that the methods of this invention could be used for the preservation and stabilization of a variety of proteins in tissue engineering applications, where denaturation of proteins may occur. Tissue engineering could be performed, e.g., for tissue regeneration, grating, transplantation, or for experimentation purposes.

It is contemplated that the methods of this invention could be used for the preservation and stabilization of a variety of proteins in cell, tissue, and organ transplantation applications, where denaturation of proteins may occur.

It is contemplated that the methods of this invention could be used for the preservation and stabilization of a variety of proteins in vitro. Nonlimiting examples of uses include the preservation of proteins in vaccines. For example, the methods of this invention provide for the storage and shipping of vaccines without refrigeration. The methods and compounds of this invention also provide for renaturation of proteins during antibody binding with other particles and/or carriers, protein/protein interaction studies, solid phase synthesis of proteins, etc.

It is contemplated that the methods and the compounds of the invention can be used for proper folding of recombinant proteins that have been produced using a variety of translation vehicles (e.g., bacteria, insects, etc.).

It is also contemplated that the present invention provides for methods of preservation of proteins in applications involving microarrays. For example, proteins in a variety of protein microarrays and tissue microarrays could be stabilized and/or renatured.

EXAMPLES

Poloxamers Renature Heat-Denatured Proteins

A standard lysozyme activity assay was used to examine the effect of poloxamers on refolding of heat-denatured proteins. Heat denatured hen egg white lysozyme (HEWL) has been extensively used as a model protein for protein folding research, and was thus used for these studies of recovery of the catalytic activity of heat-denatured enzymes.

HEWL at a concentration of 50 μM was heated at 90° C. for 40 min and then cooled to 25° C. for 30 min. The resulting solution was then treated with the non-ionic triblock copolymer poloxamer 188 (P188, MW of 8400). For comparison, some samples of heat-denatured HEWL were treated with polyethylene glycol (PEG, MW 8000). The assays were begun as quickly as possible (within 3-4 min). Enzymatic activity was measured by following spectrophotometrically the lysis of *Micrococcus lysodeikticus* (MCLD) cells.

Figure 2:
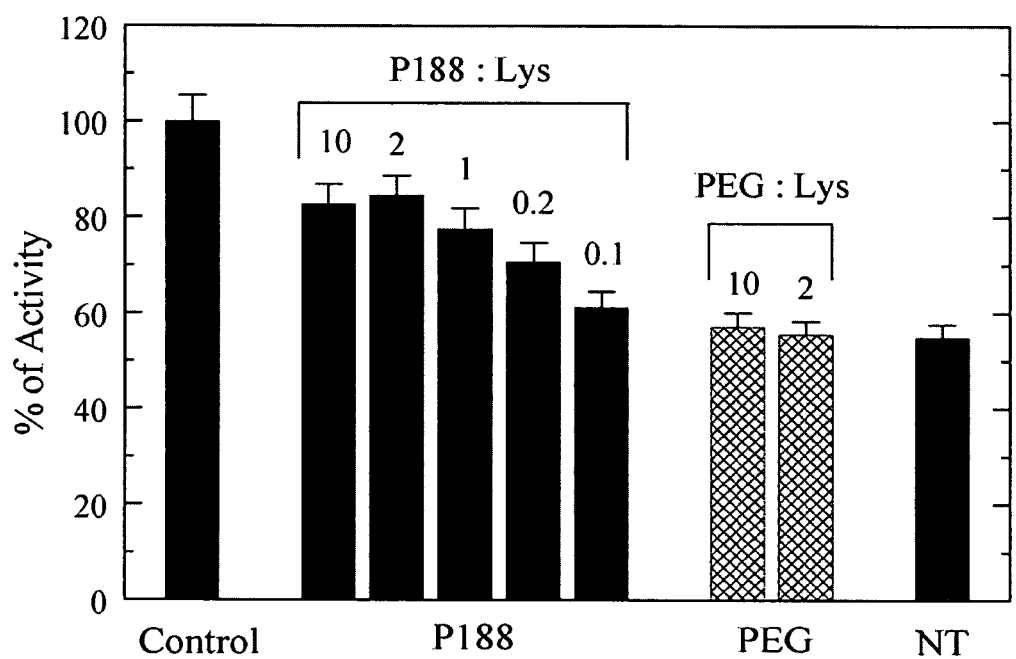
FIG. 2 shows the relative fractions of recovered enzymatic activity of heat-denatured HEWL upon addition of P188 surfactant or PEG at various molar ratios. The hydrolytic activity of HEWL was measured as described in FIG. 1. Error bars indicate standard deviations of the measurements with the numbers above each bar indicating the molar ratio of P188 or PEG with respect to HEWL. As indicated in FIG. 1, in separate runs that ratio was varied from 10:1 to 0.1:1 of P188: HEWL. Polyethylene glycol (PEG) was used in ratios of either 10:1 or 2:1 (PEG:HEWL). NT indicates no treatment.

FIG. 1 illustrates velocity data for the turbidimetric determination of the HEWL against MCLD. The poloxamer P188 was able to significantly increase the fraction of catalytically active HEWL, whereas PEG had no statistically significant effect (FIG. 1). In particular, addition of P188 in a 2:1 molar ratio resulted in full recovery of the catalytic activity of HEWL. In contrast, only 58% of the catalytic activity was recovered in untreated samples (FIG. 2).

The refolding assays were expanded to include measurement of the enzymatic activity of heat-denatured TEM-1 β-lactamase. Essentially similar chaperone-like effects of P188 were observed, further confirming the novel use of poloxamers as protein renaturation agents.

Poloxamers Renature Chemically-Denatured Proteins

To test the effect of P188 on renaturation of chemically denatured proteins, trifluoroethanol (THF) was employed as a chaotropic or denaturing organic solvent. For this investigation, carboxypeptidase A (CPA), an important digestive enzyme, was used as the test system. Specifically, the hydrolytic reaction catalyzed by carboxypeptidase A (CPA) using the classical ester substrate O-(trans-p-chlorocinnamoyl)-L-β-phenyllactate (CICPL) was used to test for the recovery of catalytic activity by the denatured enzyme in the presence of P188. For CPA, the rate-limiting step is governed by $k_3$. Under steady-state conditions, this rate constant is the dominating factor in the expression for the catalytic rate constant $k_{cat}$ or turnover number. The steady-state kinetic parameters for the hydrolysis of CICPL catalyzed by CPA are of $k_{cat}$~70 s$^{-1}$ and $k_{cat}/K_M$~7×10$^5$ M$^{-1}$s$^{-1}$. Moreover, since this chromophoric substrate has a $\Delta\epsilon$~12,000 M$^{-1}$cm$^{-1}$ at 310 nm, the use of CICPL as the substrate provides a particularly sensitive test for recovery of catalytic activity of renaturation of the chemically denatured enzyme in the presence of P188.

Carboxypeptidase A (CPA) was purchased from Sigma (Milwaukee, Wis.). The lyophilized enzyme was dissolved in solution buffered to pH 7.5 with 0.5 M NaCl and 0.05 M HEPES. Then 20%, 25%, or 50% trifluoroethanol (TFE) was added to the native enzyme solution. Enzymatic activity was measured and compared to that of the native enzyme. The incubation time was varied up to 3 hours.

For measuring the recovery of catalytic activity by the denatured CPA, 260 μL aliquots of the enzyme solution (initial concentration 1.92×10$^{-4}$ M) was added to 240 μL buffer solution (0.5 M NaCl and 0.05 M HEPES at pH=7.5), followed by the addition of 200 μL of TFE and 300 μL water in the presence of different molar ratios of P188 at ambient temperature (~24° C.). The final concentration of the enzyme upon dilution was 5×10$^{-5}$ M in the solution mixture. The concentration of P188 was varied so as to yield enzyme:P188 mixtures in 1:10, 1:5, 1:2, 1:1, 1:0.5, and 1:0.3 molar ratios. Corresponding controls were set up in parallel by similar dilution of the enzyme but in the absence of P188. Catalytic activity was then determined by addition of 10 μL of the chemically denatured enzyme solution to a solution containing CICPL to initiate the reaction. Final concentrations of the substrate and enzyme were of 5.6×10$^{-5}$ M and 1.67×10$^{-7}$ M, respectively.

Figure 3:
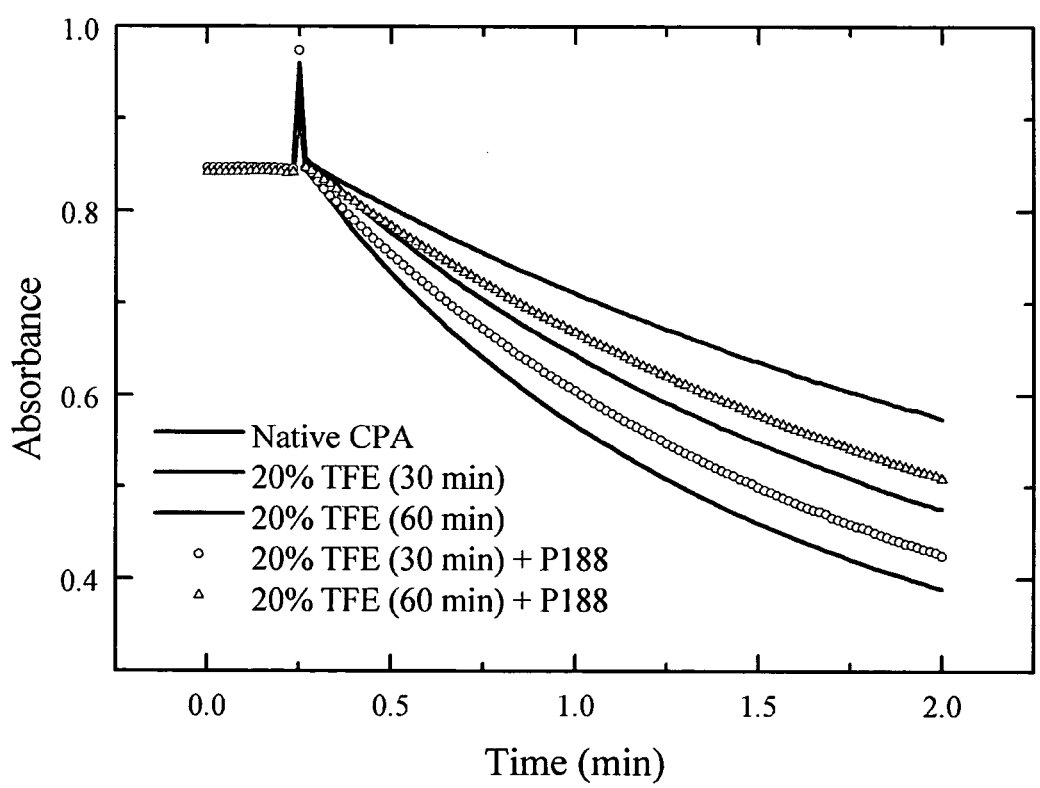
FIG. 3 shows comparison of the catalytic activity of carboxypeptidase A (CPA) denatured by 20% trifluoroethanol (TFE), in the absence or presence of P188 poloxamer, for incubation times of either 30 min or 60 min. The molar ratio of 2:1 of P188:CPA was used in these experiments.
Figure 4:
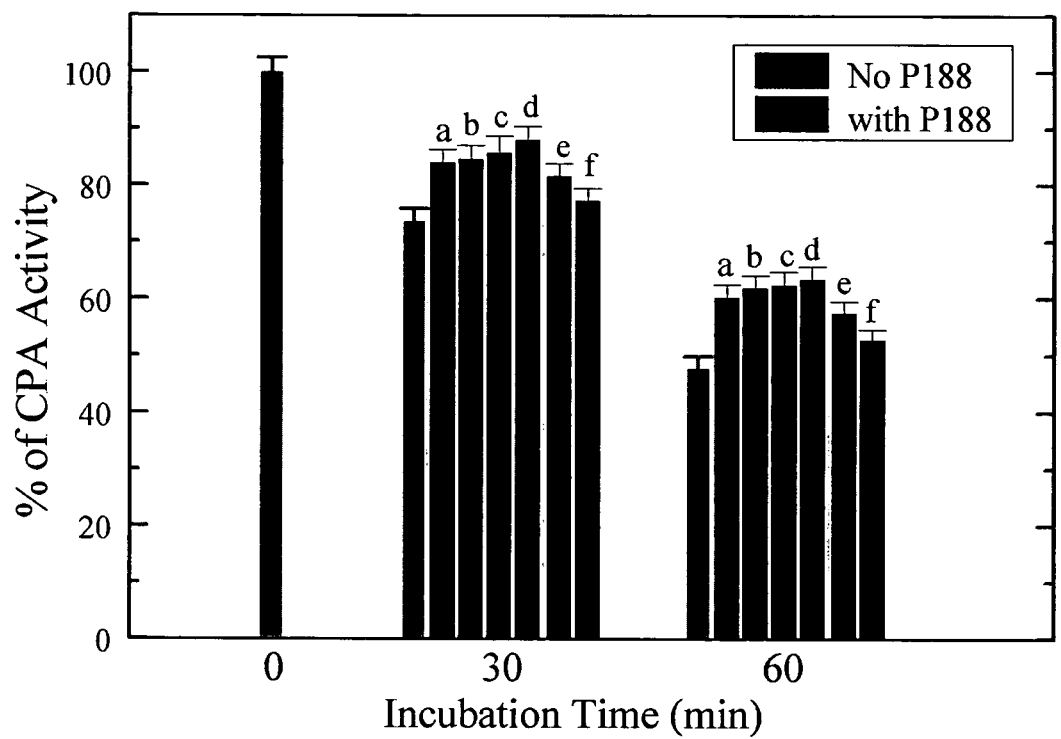
FIG. 4 shows the recoveries of the catalytic activity of carboxypeptidase A (CPA) with different molar ratios of poloxamer P188 with respect to CPA: a, 10:1; b, 5:1, c, 2:1; d, 1:1; e, 0.5:1; and f, 0.3:1 molar ratios of P188:CPA. The incubation times were either 30 min or 60 min.

FIG. 3 shows the kinetics of catalytic activity determined after a 30 and 60 min incubation period of the diluted enzyme in the presence or absence of P188. In the absence of P188, the maximum recovered activity was equivalent to only 0.7$V_{max}$ observed for the native enzyme prior to denaturation. In the presence of P188, the maximum recovered activity was observed for the enzyme:P188 mixture of 1:1. The recovery process equivalent to 0.9$V_{max}$ observed for the native enzyme prior to denaturation was complete also by 30 min. Furthermore, shown in FIG. 4 are the recoveries of the catalytic activity of CPA with different molar ratios of P188 with respect to CPA: a, 10:1; b, 5:1, c, 2:1; d, 1:1; e, 0.5:1; and f, 0.3:1 molar ratios of P188:CPA.

The results described above indicate that P188 facilitates the recovery of catalytic activity by carboxypeptidase A after denaturation of the enzyme in 20% trifluoroethanol. Thus, P188 was able to hinder the protein denaturation process resulting from the use of an organic, strong denaturing solvent. The influence of poloxamers on protein structure is measurable and has the potential for clinical applications.

The invention having been fully described, it is preferably apparent to one skilled in the art that changes and modifications can be made thereto without departing from the spirit and scope thereof.

What is claimed is:

1. A method for renaturation of a denatured protein comprising contacting a denatured protein with an aqueous solution comprising about 0.1% to 10% (w/v) poloxamer 188 at about 15° C. to about 40° C. for a time sufficient to renature the protein, wherein the denatured protein was denatured by contact with a chaotropic agent or by heating.

2. The method of claim 1 wherein the aqueous solution is buffered at about pH 6-9.

3. The method of claim 1 wherein the molar ratio of poloxamer 188 to protein is in the range of approximately 10:1 to 0.1:1.

4. The method of claim 1 wherein the molar ratio of poloxamer 188 to protein is approximately 2:1.

5. The method of claim 1 wherein the poloxamer 188 is generated by the sequential addition of two or more alkylene oxides to a low molecular weight water-soluble organic compound containing one or more active hydrogen atoms.

6. The method of claim 1 wherein renaturing of the protein is carried out for at least 0.5 hours.

7. The method of claim 1 wherein the protein is a recombinant protein.

8. The method of claim 1 wherein the protein is an antibody.

9. The method of claim 1 wherein the protein is an enzyme, and wherein at least 10% of the enzyme's native biological activity is restored.

10. A method for restoring the biological activity to a denatured protein comprising contacting a denatured protein with an aqueous solution comprising about 0.1% to 10% (w/v) poloxamer 188 at about 15° C. to about 40° C. for a time sufficient to restore at least 80% of the protein's native biological activity, wherein the denatured protein was denatured by contact with a chaotropic agent or by heating.

11. The method of claim 10 wherein the aqueous medium is buffered at about pH 6-9.

12. The method of claim 10 wherein the molar ratio of poloxamer 188 to denatured protein is in the range of approximately 10:1 to 0.1:1.

13. The method of claim 10 wherein the molar ratio of poloxamer 188 to denatured protein is approximately 2:1.

14. The method of claim 10 wherein the poloxamer 188 is prepared by the sequential addition of two or more alkylene oxides to a low molecular weight water-soluble organic compound containing one or more active hydrogen atoms.

15. The method of claim 10 wherein restoring of the biological activity is carried out for at least 0.5 hours.

16. The method of claim 10 wherein at least 95% of the protein's native biological activity is restored.

17. The method of claim 1, wherein the contacting occurs within non-animal foodstuff.

* * * * *